United States Patent
Fuechslin et al.

(10) Patent No.: US 7,614,857 B2
(45) Date of Patent: Nov. 10, 2009

(54) MEDICAL PUMP DEVICE

(75) Inventors: Rudolf Marcel Fuechslin, Brugg (CH); Markus Weiss, Bauma (CH); Rudolf Duenkl, Winterthur (CH); Peter Fritz Mejer, Aarau (CH); Thomas Neff, Maennedorf (CH); Erich Paul Stoll, Stallikon (CH); Andreas Suter, Nussbaumen (CH)

(73) Assignee: Medinnovation AG, Zurich (CH)

( * ) Notice: Subject to any disclaimer, the term of this patent is extended or adjusted under 35 U.S.C. 154(b) by 182 days.

(21) Appl. No.: 10/495,462

(22) PCT Filed: Nov. 15, 2002

(86) PCT No.: PCT/IB02/04771

§ 371 (c)(1),
(2), (4) Date: Aug. 27, 2004

(87) PCT Pub. No.: WO03/041767

PCT Pub. Date: May 22, 2003

(65) Prior Publication Data
US 2005/0002806 A1  Jan. 6, 2005

(30) Foreign Application Priority Data
Nov. 16, 2001  (CH) ..................... 2110/01
May 22, 2002  (CH) ..................... 0857/02

(51) Int. Cl.
*F04B 7/00* (2006.01)
(52) U.S. Cl. ............... 417/519; 417/506; 417/509; 137/625.47; 604/32; 604/248
(58) Field of Classification Search .......... 417/506, 417/519, 509; 604/32, 248; 137/624.16, 137/624.17, 624.18, 625.47
See application file for complete search history.

(56) References Cited

U.S. PATENT DOCUMENTS

| 4,173,234 | A | * | 11/1979 | Thomas et al. | ......... 137/625.47 |
|---|---|---|---|---|---|
| 4,273,121 | A | | 6/1981 | Jassawalla | ................. 128/214 |
| 4,702,269 | A | * | 10/1987 | Schuler | ................. 137/246.12 |
| 4,767,399 | A | * | 8/1988 | Bollish | ................. 604/6.06 |
| 4,798,589 | A | * | 1/1989 | Tseo | ................. 604/152 |
| 4,850,980 | A | * | 7/1989 | Lentz et al. | ................. 604/248 |
| 5,072,758 | A | * | 12/1991 | Krambrock | ................. 137/625.47 |
| 5,443,453 | A | * | 8/1995 | Walker et al. | ................. 604/248 |
| 5,713,850 | A | * | 2/1998 | Heilmann et al. | ................. 604/28 |
| 5,916,201 | A | * | 6/1999 | Wilson et al. | ................. 604/248 |
| 5,993,654 | A | * | 11/1999 | Black | ................. 210/198.2 |
| 6,213,723 | B1 | | 4/2001 | Danby et al. | ................. 417/53 |

(Continued)

FOREIGN PATENT DOCUMENTS

DE    19 909 654    7/2002

(Continued)

*Primary Examiner*—Devon C Kramer
*Assistant Examiner*—Leonard J Weinstein
(74) *Attorney, Agent, or Firm*—Kenyon & Kenyon LLP

(57) ABSTRACT

The invention relates to a medical pump device comprising a rotary valve (13) having preferably only one rectilinear channel (20) which respectively connects the inlet (4) and the outlet (7) of the pump device, or connects the inlet to a pump chamber (15), or said pump chamber to the outlet, upon rotation of the rotary element (19) of the valve. The invention enables a medical pump device to be especially easily produced, said pump device being preferably inserted between an infusion syringe driver or an infusion container and a catheter, and being used to supply small quantities of liquid in an accurately dosed manner.

8 Claims, 12 Drawing Sheets

U.S. PATENT DOCUMENTS 6,626,884 B1 * 9/2003 Dillon et al. ................ 604/409

FOREIGN PATENT DOCUMENTS

| | | |
|---|---|---|
| EP | 0 345 396 | 12/1989 |
| EP | 1 020 203 | 7/2000 |
| GB | 2 060 131 | 4/1981 |
| GB | 2 157 374 | 10/1985 |

* cited by examiner

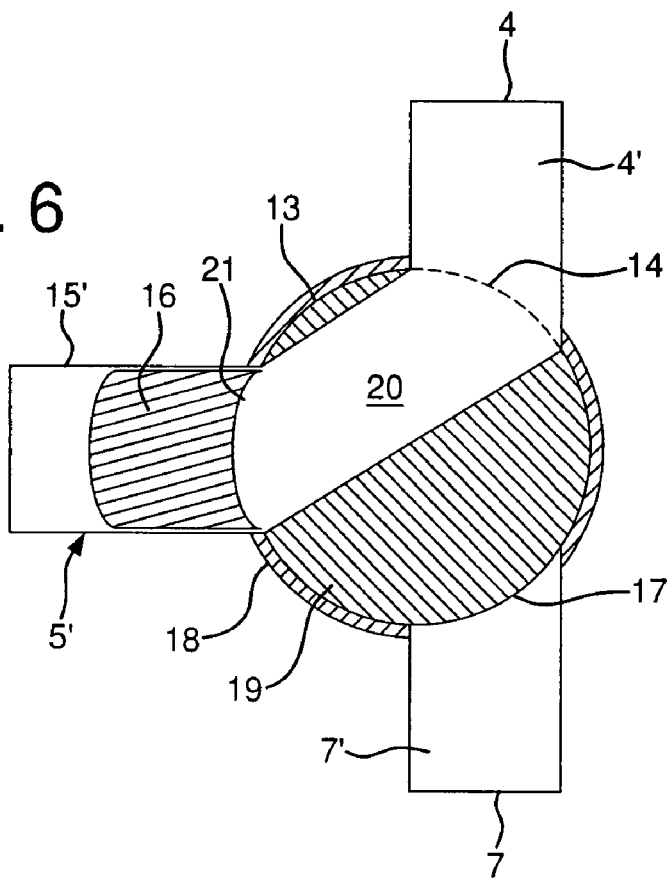
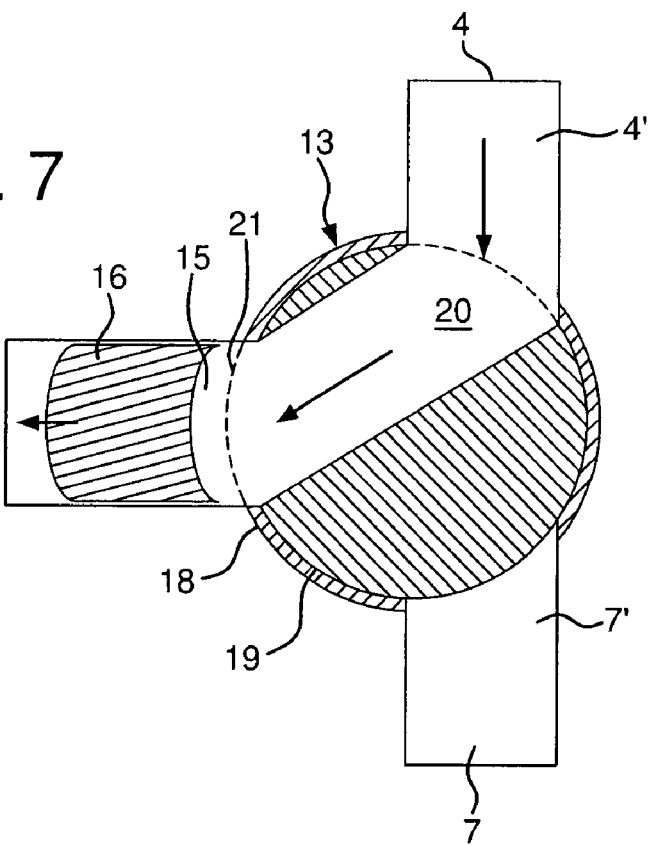

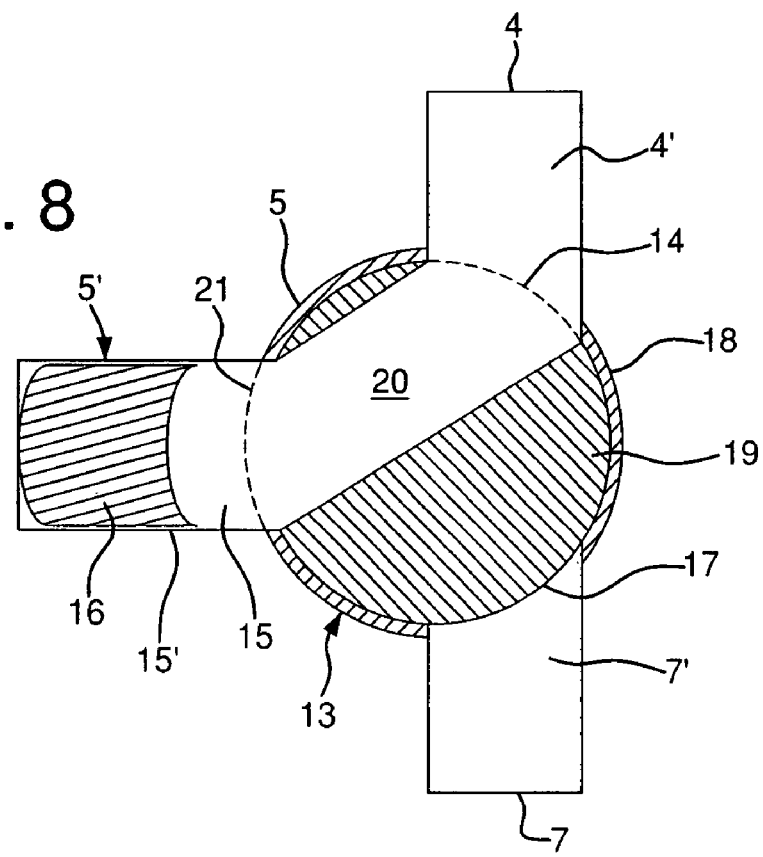
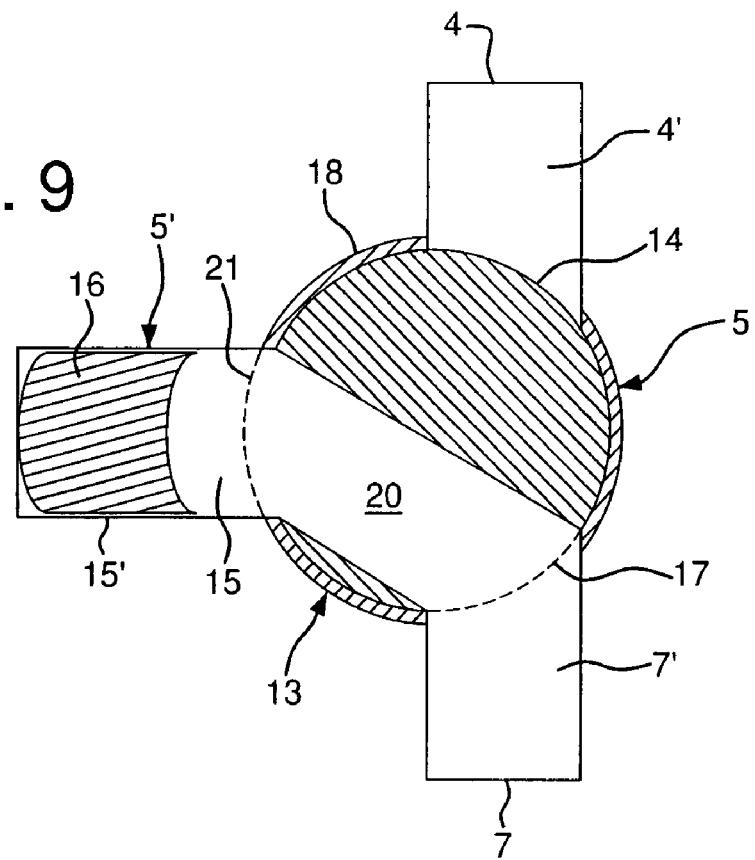

MEDICAL PUMP DEVICE

REFERENCE TO RELATED APPLICATIONS

This application is a 371 national phase of PCT/IB02/04771 filed on 15 Nov. 2002, the content of which is incorporated herein by reference in its entirety.

This application claims the priority of the Swiss patent application No. 2110/01 of Nov. 16, 2001 and the Swiss patent application No. 857/02 of May 27, 2002, of which the contents shall be considered incorporated in the disclosure of the present application by reference thereto.

TECHNICAL FIELD

The invention relates to a medical pump device according to the introductory portions of the claims 1, 2 and 11. The invention relates further to a pump system according to claim 12.

PRIOR ART

For a continuous application of liquids or medicines infusion pumps and injection pumps are used. Whereas liquids are fed at infusion pumps by means of a squeegee acting onto a hose, the medical solution is ejected at the injection pump by a displacing of the piston of the syringe. At the latter system the amount of the ejected medicament is a function of the position of the piston. Injection pump systems are predominantly used in order to continuously administer potent medicaments as a highly concentrated solution at low mass flows.

In specifically the pediatric intensive medicine the process proceeds with very low mass flows in order not to burden the patient unnecessarily with liquids. Overly large fluctuations of the mass flow could be perilous in case of use of highly concentrated potent, short-time active medicaments.

Injection pumps systems are in case of low mass flows quite sensitive to hydrostatic pressure changes (lifting/lowering the pump) due to the resilience of pump, syringe (specifically piston rubber), air in the liquid solution and infusion conduit [literature 1,2 according to literature table at end of the description]. Elastic deformations and momentary jamming (sticking-effect) lead to the situation that no precise relation between position of the piston and ejected volume exists. A vertical lowering of the injection pump can, due to the change of the hydrostatic pressure conditions lead to siphon effects with a retrograde flow and zero medicament application time. This becomes especially at low mass flows (<1 ml/h) significant. Conversely, a raising of the pump can lead to a depleting (infusion bolus) of the expandable elements [3,4].

In case of a closure or a buckling of the conduit the expandable elements retard the pressure building in the infusion system and accordingly the closure alarm [10-12].

The in-depth analysis of the individual components has revealed that the main portion of the resiliency stems predominantly from the syringe pump, the infusion syringe and the air [5-9, 12].

It could be evidenced, thereby, that the resilience of thin, stiff infusion conduits is vastly lower than the one of the reservoir, i.e. the pump and the syringe.

Infusion pumps, at the other hand, such as known e.g. by the U.S. Pat. No. 6,213,723 are as a rule less suitable for the application of highly concentrated, short-time active medicaments at low mass flows. The placing of the proximal squeegee prior to the disengaging of the distal squeegee leads to a pressure rise in the infusion conduit, which upon a disengaging of the distal squeegee leads to a momentary high mass flow. The infusion systems used thereto are highly resilient and accordingly quite sensible to hydrostatic changes. Both infusion systems have the drawback that they provide no control over the actual precisely dispensed amount of liquid [13-16].

Furthermore, a cassette-pump is disclosed by the U.S. Pat. No. 4,273,121 which is placed between a infusion container and the catheter or patient, respectively. The cassette comprises a chamber delimited by a membrane, whereby the pressure action onto the membrane allows in cooperation with hose clamps arranged at the inlet and the outlet and acting as valves the pumping of small volumina in the direction of the patient. Because, however, at this pump up to 75% of the resilient membrane surface is exposed and not acted upon by the associated piston, there results also a considerable dependency of this cassette pump from the inlet pressure of the liquid and, thus, the height position of the infusion container. A cooperation with a injection pump for supplying the cassette pump is not mentioned and appears not advantageous due to the resiliency and corresponding position dependency of both pumps.

By the CH-patent application No. 2110/01 a pump device and a pump system are known which can obviate the mentioned drawbacks.

SUMMARY OF THE INVENTION

The invention is based on the object to provide a pump device and a pump system which are of a especially simple design.

This is attained by a pump device of the kind mentioned above with the features of the claims 1, 2 and 11 and with a pump system according to claim 12, as well.

By the rotary valve with preferably uniformly distributed connections and pump chamber a very simple design is arrived at. The preferably single rectilinear channel allows a safe rinsing of the device and avoids projections on which air bubbles can grow.

By the preferred rigid design of the pump chamber the pump system can deliver always the same pump volume independent from inlet pressure fluctuations; corresponding situations are true for the pump systems in which the resiliency of the infusion syringe and the driver have no longer a influence on the delivered pump volume.

At a preferred embodiment the rigid but moveable chamber wall is formed by a rigid piston or plunger. At a different embodiment the rigid chamber wall is formed by a as such elastic or quasi-elastic membrane. It can be acted upon completely by a rigid actuation means, preferably a liquid, so that the membrane acts also as a rigid element which yields only as far as the incompressible actuation means allows such, so that it is possible to pump at constant volume. As quasi-elastic membrane a membrane is understood of which the expansion is limited by a reinforcement.

Accordingly, a infusion system with a minimal resilience is arrived at which allows to control the dispensed amount of liquid. To this end a preferably not expandable, micro-volumetric controllable infusion driver is switched in between expandable driver with infusion syringe or infusion container and basically not expandable infusion conduit. In principle, small volumina of a accurate size V and a minimal resilience are cyclically filled and completely drained. The totally administered amount of medicament is then known at any point of time up to a volume V. The drainings of the volumina V can be counted. The pumping process is discretized. Only two sources can have imprecisenesses. Firstly, one can be just in a draining process which leads a maximal impreciseness of V. In the proposed preferred realisation V amounts to 1-10 mm$^3$ which reduces the mentioned impreciseness to be medicinally unimportant measure. Secondly, one has a additive, i.e. with the time growing impreciseness due to the resiliency of the volumina V themselves. This is, however, presupposed in the following suggested systems to be small.

The proposed principle allows specifically to reduce to a large extent volume effects which are caused by changes of the hydrostatic pressure, because the feed of the liquid is no longer set basically by the applied pressure to a larger volume, but rather by the number of drainages of the volumina V.

The proposed infusion systems includes basically a liquid reservoir, a infusion driver (volume discretisator) and a following rigid infusion conduit, whereby the liquid reservoir is subject to a slight pressure due to the vertical height or a tension spring. The infusion driver consists preferably of a disposable plastic part, a re-usable driver part and control unit.

The device for a volume controlled pumping of a liquid medium in the field of medical applications allows, thus, the controlling of the mass flow by a discretising of the drainable liquid volume by use of cyclically fillable and drainable volumina with a precisely defined content. The position of the device is somewhere in the conduit between reservoir and patient. Preferred is a bypass function for the venting of the system. Preferred is the separation of the device into once usable chamber components and multiply usable components (driver, control). Preferably control elements (e.g. air detectors, pressure sensors) are employed for the monitoring of the proper function of the device. The reservoir is realized by infusion bag, bottle or preferably by a syringe driver or a pressurized infusion syringe, respectively. By the pump device according to the invention the demand made on accuracy of the reservoir or the reservoir draining mechanism, respectively which serves now merely for the filling of the pump device is, thereby, considerably lowered.

BRIEF DESCRIPTION OF THE DRAWINGS

In the following embodiments of the invention are explained in detail with reference to the drawings. Thereby there is illustrated in FIG. 1 schematically the arrangement of the pump device at a infusion syringe driver;

FIG. 6 a embodiment of FIG. 4 in the position of filling the pump chamber;

FIG. 7 the filling of the pump chamber with a first piston position;

FIG. 8 a further piston position;

FIG. 9 the position for draining the pump chamber;

DETAILED DESCRIPTION

Figure 1:
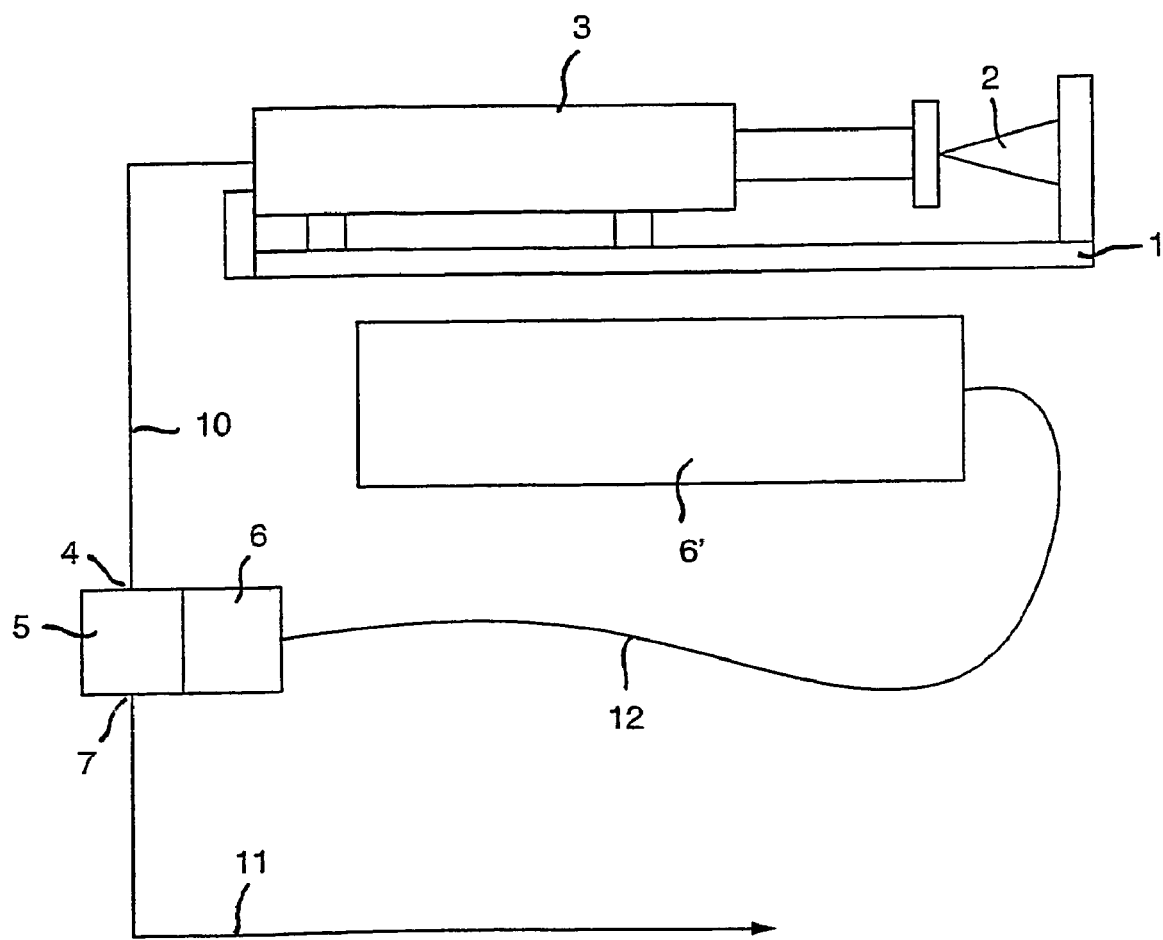

FIG. 1 illustrates rough schematically the preferred use of the medical pump device or the pump system, respectively. It includes at the one hand a as such known infusion syringe driver with a infusion syringe slide 1 which can receive a infusion syringe 3 which is operated by a syringe driver 2 (in the simplest case a spring), so that a ejecting of the liquid in the infusion syringe 3 occurs with a predetermined amount per time unit (motor) or a relatively constant pressure (spring). Corresponding infusion syringe drivers are known and are not explained herein in detail. According to the prior art the outlet of the syringe pump 1 is directly coupled to the patient, or supplies a catheter, respectively. According to the invention a pump system is now provided in which the infusion syringe 3 serves merely for supplying the pump device 4-7 through the conduit 10. The conduit 10 runs, thereby, from the outlet of the syringe pump 1 to a inlet connector 4 of the pump device 4-7. A conduit 11 which runs to the patient is in turn connected to the outlet connector of the pump device. In the illustrated schematic form the pump device includes the pump unit 5 proper, as well as a driving unit 6 arranged separable from same which drives the pump unit proper. The signification of this preferred separation is that the pump unit 5 can be exchanged for each respective application through a new one intended for a single use and the driving unit 6 can be kept. In the illustrated example the driving unit 6 is operated by a not in detail illustrated control and indicator unit 6' which controls the driving unit through a control conduit 12. The desired mass flow of feed of the pump device 4-7 can be set and displayed at the control unit 6'. This illustrated embodiment with separate units is obviously to be understood only as example and a pump device could be foreseen as only one unit which unites the parts 4, 5, 6 and 6'. The pump system illustrated in FIG. 1 does not feature the drawbacks of known syringe pumps which are mentioned in the investigations according to the bibliography because the pump device 4-7 can avoid the problems with the resilience or sensitivity to hydraulic pressure changes and other drawbacks of the arrangement of syringe and its operating device. The pump device 4-7 of the system ensures that substantially independent from inlet pressure fluctuations always the same volume per unit of time is fed.

Figure 2:
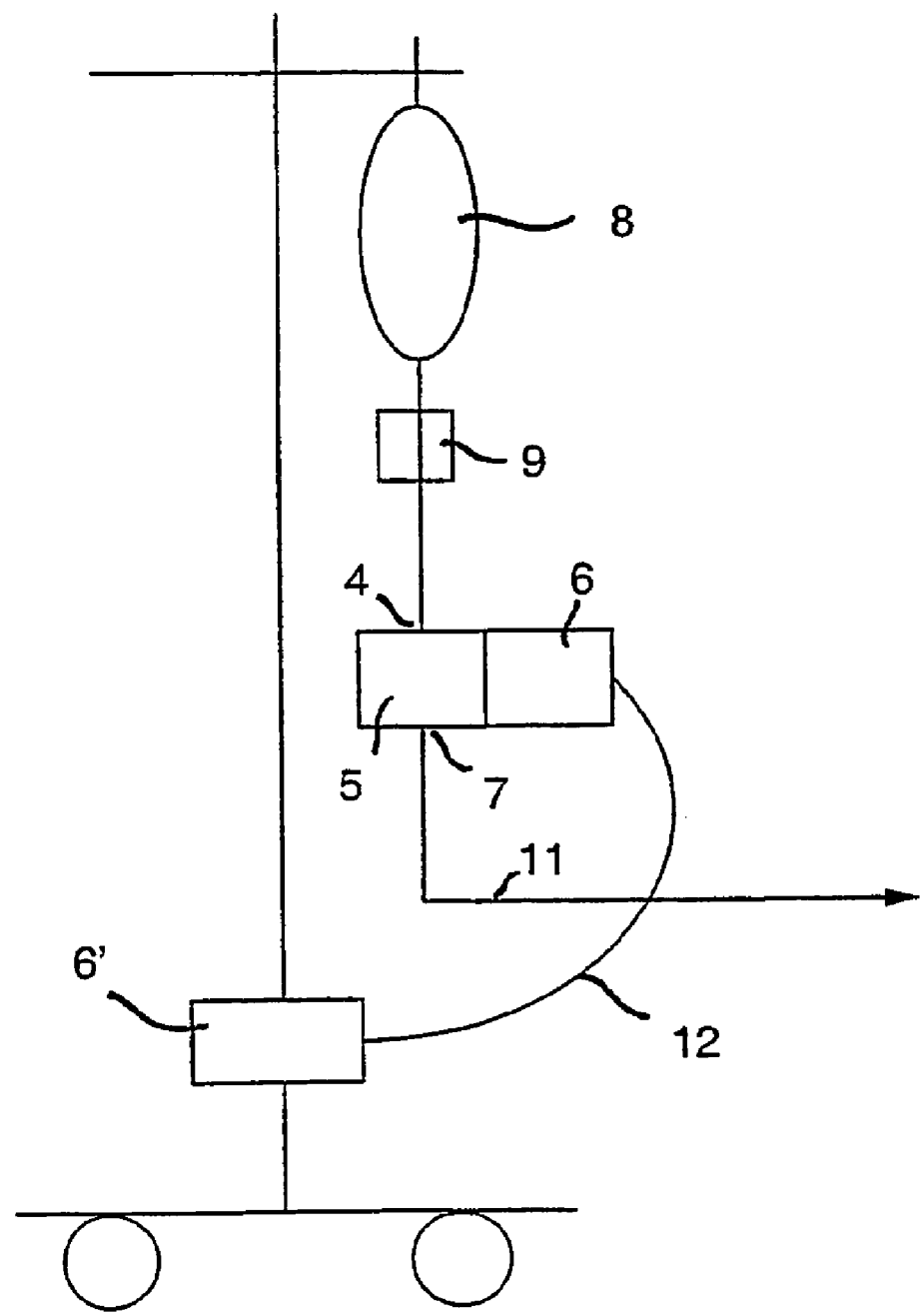
FIG. 2 the arrangement of the pump device at a infusion bottle or a infusion bag.

Similar advantages arise if, such as illustrated in FIG. 2, the medical pump device 4-7 can be connected downstream at the outlet of a conventionable infusion container 8 which may be followed by a droplet chamber 9. Also in this case the conduit 10 runs to the inlet connector 4 of the pump device 4-7 and the conduit 11 runs from the outlet connector 7 of the pump device to the patient. In the following, various pump devices are explained with reference to more or less schematic illustrations, whereby as a rule only the pump unit 5 proper is illustrated and the driving unit 6 as well as the control and display unit 6' are not illustrated. The design of the respective driving unit 6 is determined by the movement of the piston and of the rotary element in the pump unit 5 which is still to be described and can, therefore, be realized by the person skilled in the art in various ways without any further instructions in the bounds of its technical knowledge. Thereby, electromotors can be used as linear motors, step motors or conventional motors with gear units. Also pneumatic or hydraulic drives are possible. The respective control and display unit 6' is also designed in a manner basically known to the person skilled in the art in a electronic, preferably microprocessor controlled form and must not be explained here more in detail. Because in accordance with the invention the pumped volume of every pumping operation step can be considered as being constant, a simple setting and controlling of the mass flow is specifically possible by a setting and counting of the strokes of the pump. In the following embodiments same elements such as in the FIGS. 1 and 2 are identified in these Figures basically by the same reference numerals.

Figure 4:
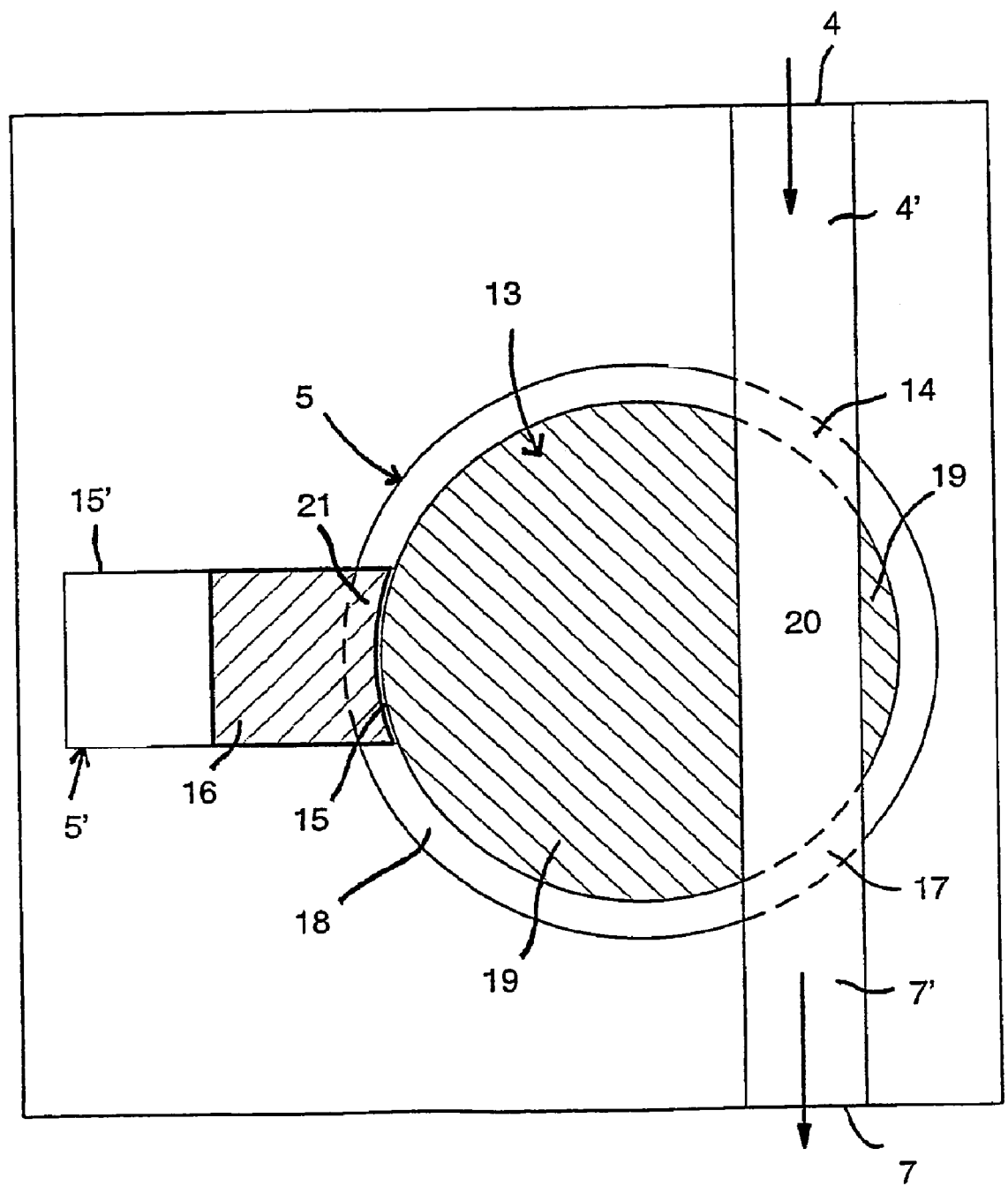
FIG. 4 roughly schematically the pump device without driving elements in the rinsing position.

FIG. 4 shows in a partially horizontally cut schematic illustration the pump device in a top view with the cover removed, which pump device is depicted generally only by the border which is, however, for sake of simplicity not used in the further Figures. The device includes a inlet connector 4 to which the already mentioned conduit 10 of the syringe pump or of a infusion container may be connected. The corresponding connecting means are not illustrated; such may be any known connecting means. The device includes, furthermore, a outlet connector 7 to which the mentioned conduit 11 can be connected in the same manner. The pump device has, thereby, connectors for the illustrated infusion conduits (distal and proximal) or has itself short conduits for the infusion conduit (distal and proximal) or includes already connected, e.g. welded infusion conduits, e.g. also the proximal conduit with a droplet chamber at the bag system, or a combination of these connecting variants if foreseen. The device includes, furthermore, the pump unit 5 proper, as well as the driving unit and control unit not illustrated in FIG. 4. The pump device includes now a multiway valve 13 which is switchable by a rotary movement, which includes in a cylinder shaped valve housing 18 a rotatable, cylinder shaped valve element 19 which comprises a channel 20. The channel 20 extends, thereby, in the element 19 at its illustrated position from the opening 14 in the housing 18 to the opening 17 in the housing 18, whereby the channel with e.g. a cylinder shaped or square cross section is aligned with the corresponding openings in the housing 18, so that the liquid can flow from the inlet connector 4 through a possibly only very short or even not present conduit portion 4' through the opening 14 of the housing, the channel 20 and through a opening 17 of the housing and through the possibly very short or not present conduit portion 7' to the outlet connector 7 of the pump device when the valve element 19 is in the illustrated position. The drawing is, thereby, kept simple so that the conduit portions 4' and 7' form together with the channel 20 one unit in the Figure, which obviously is not the case, because these conduit portions 4' and 7' and the channel 20 are separate sections which are aligned in the illustrated position of the rotary element 19. The wall of a chamber is identified by 15', in which a rigid but displaceable piston 16 is arranged. These parts form the pump portion 5' proper. Through a housing opening 21 in the housing 18 the chamber is open towards the element 19, whereby in the illustrated position it communicates neither with the inlet connector 4 nor with the outlet connector 7 and the piston 16 is in its forward end position. At this position of the piston the chamber 15 between the front end of the piston and the opening 21 of the housing possesses practically no volume. Inlet, outlet and the chamber, and the openings 14, 17 and 21, respectively are distributed uniformly around the rotary valve housing, thus at a respective angular distance of 120°. The piston includes preferably the illustrated, hollow dished front end at the housing opening 21 which front end is made to conform to the cylinder shaped outer contour of the element 19.

In the illustrated position of the pump device a liquid flow from the syringe pump or the infusion container, respectively through the device is possible, which allows a rinsing of the device. The preferably rectilinear extending channel 20 has, thereby, not edges and projections onto which air bubbles could adhere. It is also preferred that the channel is aligned with the inlet 4 and outlet 7, respectively in such a manner that no edges and projections are formed.

Figure 5:
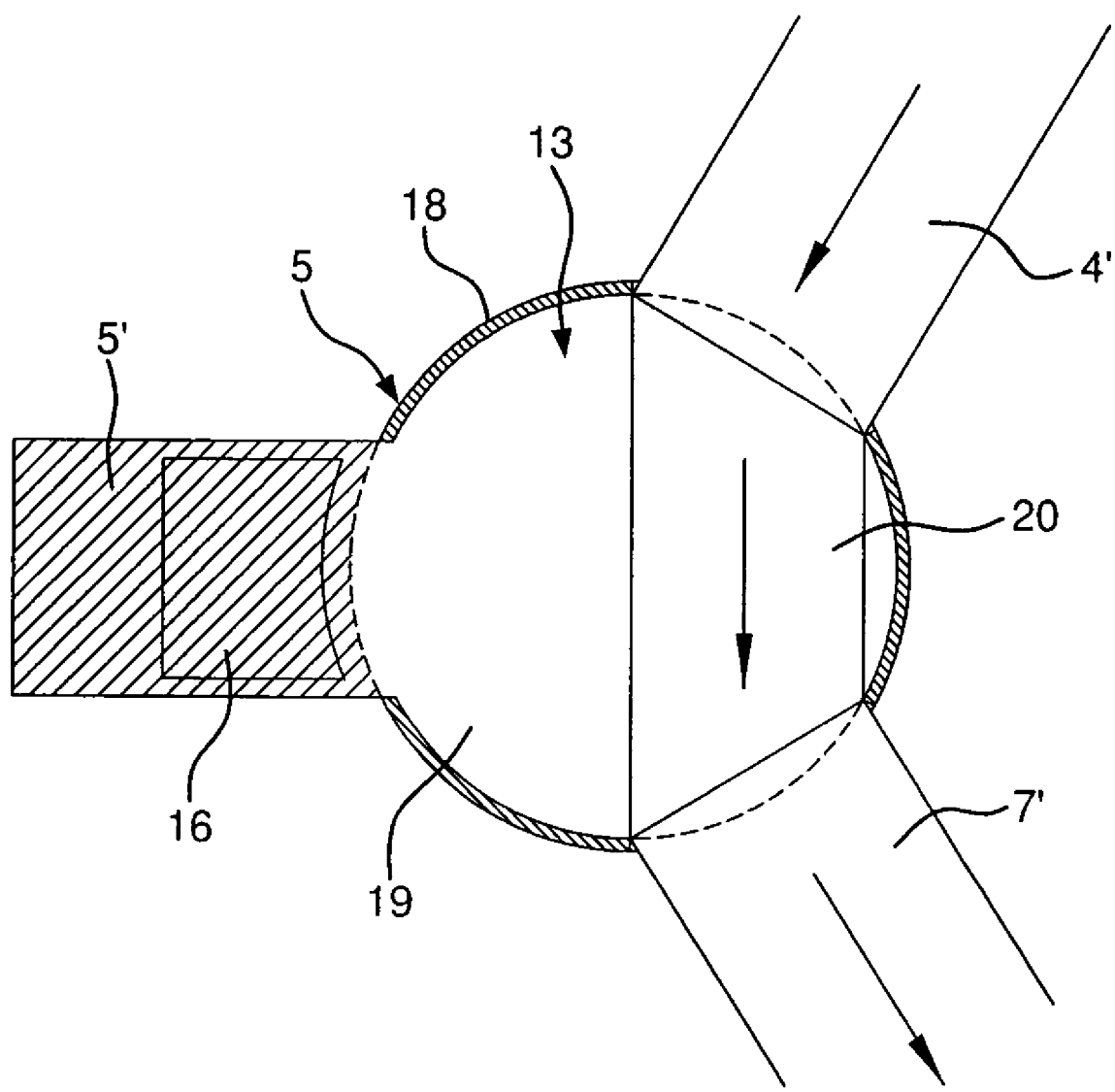
FIG. 5 a embodiment of the pump device also in the rinsing position.

FIG. 5 illustrates a modified embodiment, in which again the same reference numerals as in FIG. 4 denote basically the same elements. In this case the conduit portions 4' and 7' are arranged at an angle to the channel course 20. In other respects the pump device remains basically the same. In FIG. 5 the pump portion is identified only generally by the reference numeral 5' without the piston and chamber being illustrated more precisely. Also the housing openings 14 and 17 are only denoted. The conduit portions 4' and 7' can also be completely omitted in FIG. 4 as well as in FIG. 5 if the inlet connector 4 and the outlet connector 7, respectively are formed directly on the housing 18 of the rotary valve 12. In such event the conduit portion 4', 7' may be only very short pipe stubs. The bypass position illustrated in the FIGS. 4 and 5, by which the pump device or pump system, respectively can be rinsed by infusion solution serves, as mentioned, for a rinsing or allowing air bubbles to rise. Latter is especially relevant if a droplet chamber is used above the pump device such as conventional when using a infusion container. A joggling functional (fine vibrations) of the pump device in the bypass position can expedite the rising of air bubbles.

During the pumping operation proper, which will be explained later on, thy bypass position is no longer taken, so that thereby no direct communication between inlet and outlet exists.

FIG. 6 illustrates now the aspirating position of the pump device according to FIG. 4 in which the element 19 of the rotary valve has been rotated in such a manner that the channel 20 connects the inlet connector 4 with the pump part 5'. The channel 20 will come to be positioned, thereby, in such a manner that it connects the housing opening 14 to the housing opening 21 of the valve housing 18 and accordingly allows entry of liquid into the chamber of the pump part 5'. FIG. 7 illustrates a resulting position in which the flow of liquid proceeds into the chamber, whereby the piston 16 is pushed back by the pressure of the liquid or, preferably, is moved back by a driving means of the not illustrated driving unit 6. In this position of the element 19, the conduit 7' or outlet connector 7, respectively, are blocked and not supplied by liquid. This position can, therefore, be also used as blocking position (occlusion position) of the pump device should the liquid flow be blocked by a corresponding positioning of the pump device. FIG. 8 illustrates the completed filling of the chamber of the pump in which the piston 16 is located in its rear dead center position. The amount of liquid present in the chamber or the amount of liquid which can be expelled is thereby e.g. in the range of 0.001 ml to 0.01 ml which corresponds to a volume of 1 $mm^3$ to 10 $mm^3$, whereby the ejectable amount is determined by the cross-section of the space in which the chamber is formed and the stroke of the piston which defines the length of the chamber. The indicated range is a preferred range for the pump volume of the present medical pump device and is regarded also as preferred range for the further variants mention in this specification. A fine vibrating (e.g. by means of the driving unit 6) can also be produced at the aspiration position in order to cause air bubbles (micro-air bubbles) to rise upwards.

Figure 10:
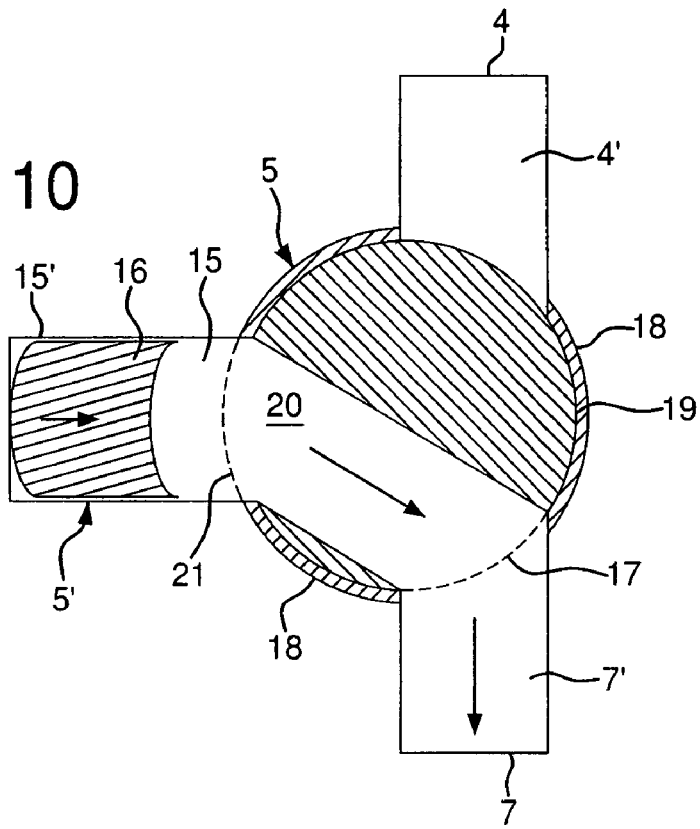
FIG. 10 a piston position during the draining.
Figure 11:
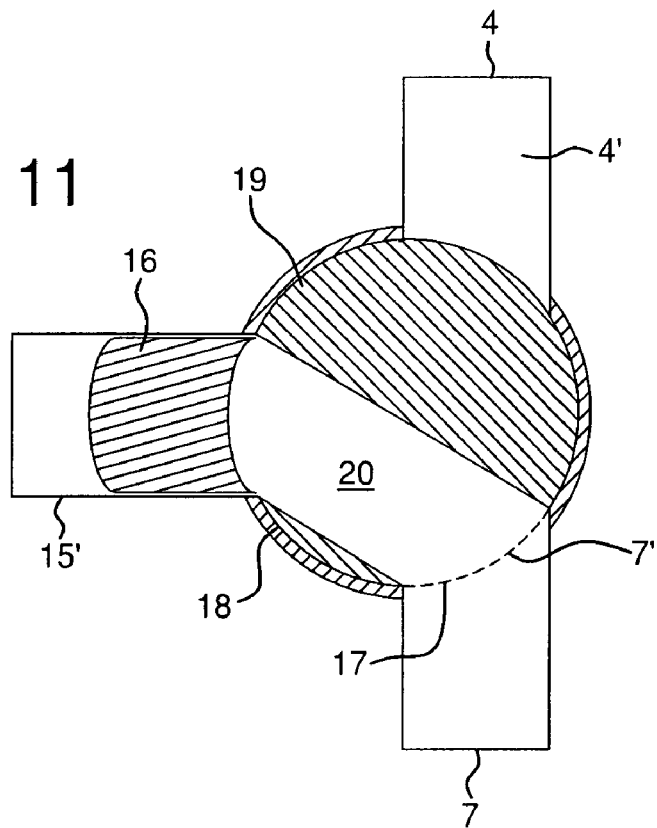
FIG. 11 the end of the draining of the pump chamber.

After according the chamber has been filled the rotatable valve element 19 is rotated further in the not-blocking operation of the pump device, so that the channel 20 connects the opening 21 of the chamber with the opening 17 such as illustrated in FIG. 9. In this ejection position the further entry of liquid through the inlet connector 4 and the conduit stub 4' is blocked by the element 19. The FIGS. 10 and 11 illustrate now the pumping process proper, in which the piston 16 is moved by the not illustrated drive unit towards the opening 21 of the valve housing 18, wherewith the liquid present in the chamber is expulsed from same and is discharged through the outlet connector 7 of the pump device. FIG. 11 illustrates the corresponding end position in which the entire chamber volume of liquid has been ejected. Also this position can be used as blocking position of the pump device (occlusion position) if the pump has been set correspondingly by the operator that no liquid shall be pumped.

Figure 12:
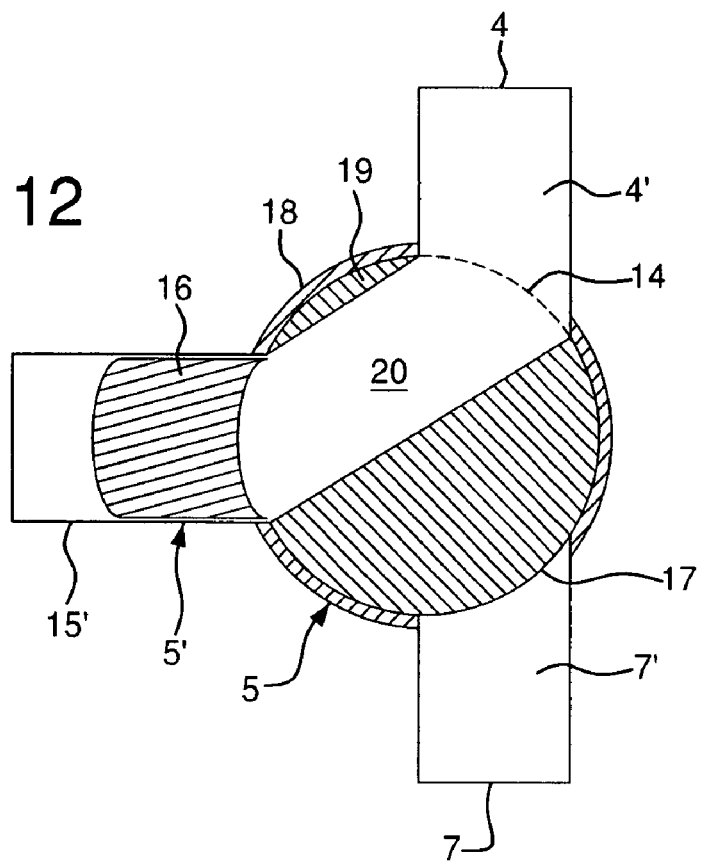
FIG. 12 the position for a anewed filling.

Contrary thereto, if in the actual pumping operation following the position of FIG. 11 a rotation of the valve element 19 by the not illustrated driving unit and the not illustrated control unit is made so that a anewed filling of the pump chambers from the inlet side (inlet connector 4) of the pump device can be reached. After a complete filling of the chamber again the position according to FIGS. 9 to 11 is passed through, at which the ejecting occurs, whereafter again the filling position according to FIG. 12 or FIGS. 6 and 7, respectively is obtained. In this way a continuous filling and emptying of the pump chamber of the pump unit 5 is reached, wherewith the pump device feeds in the desired way the small amounts of liquid. At the end of the desired operation time again one of the positions can than be maintained as occlusion position.

The foreseeing of the rotary valve 13 with the preferably rectiliniear channel 20 leads thereby to a very simple design which is also driveable by a correspondingly simple drive unit. Contrary to the as such known three-way valves in which T-shaped or L-shaped channels are foreseen in the stop cock, only one channel is used in the illustrated valve 13 which either allows the rinsing such as illustrated in the FIGS. 4 and 5 and allows thereafter by the alternating other two positions the filling and emptying of the pump chamber or blocks in one of these two positions at the switched off driving unit the through-flow through the pump. T- or L-shaped three-way cocks would not allow to provide a direct bypass connection and would incorporate the risk of the forming of accumulations of air.

Figure 13:
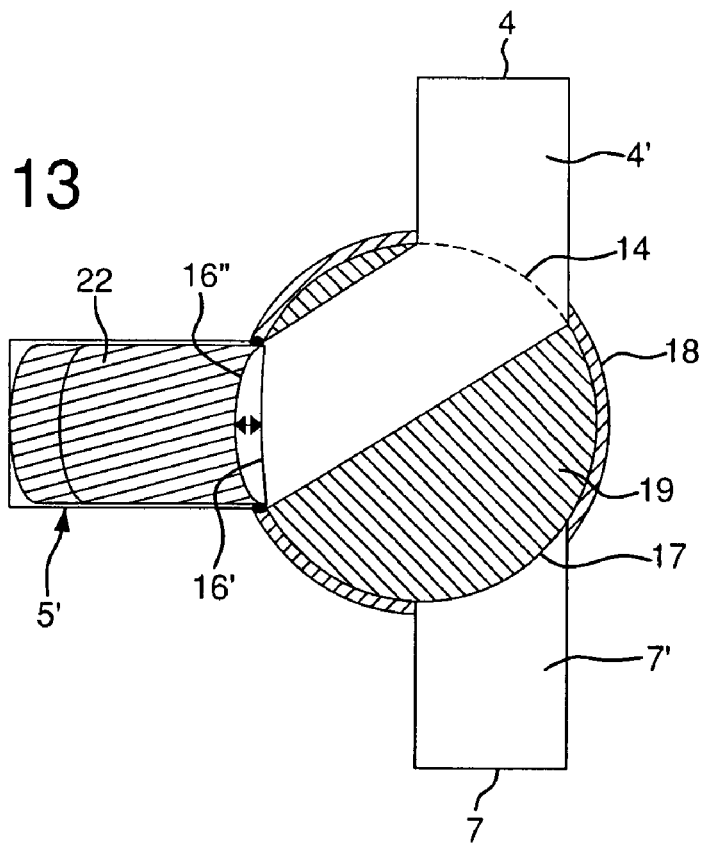
FIG. 13 a further embodiment of the pump device in a pump chamber filling position.

FIG. 13 illustrates a variant with the basically same rotary valve 13, in which, however, the pump part 5' comprises in place of a piston a elastic or quasi elastic body, e.g. a membrane 16' which can be deformed by the pressure of the liquid so that a set chamber volume is filled. In FIG. 13 the membrane is identified thereby once in its rest state by 16' and in its partly or completely filled state by 16". A e.g. liquid 22 may be arranged behind the membrane, which allows only a certain deformation of the membrane. Corresponding arrangements are known through the CH-patent application No. 2110/01 the content of which shall be considered herein, completely included by reference thereto. The membrane 16' is mounted preferably all around along the circumference of the housing opening 21 so that a uniform space for the liquid to be received is arrived at and it can be done without seals and sliding spaces for the piston cylinder.

Figure 3:
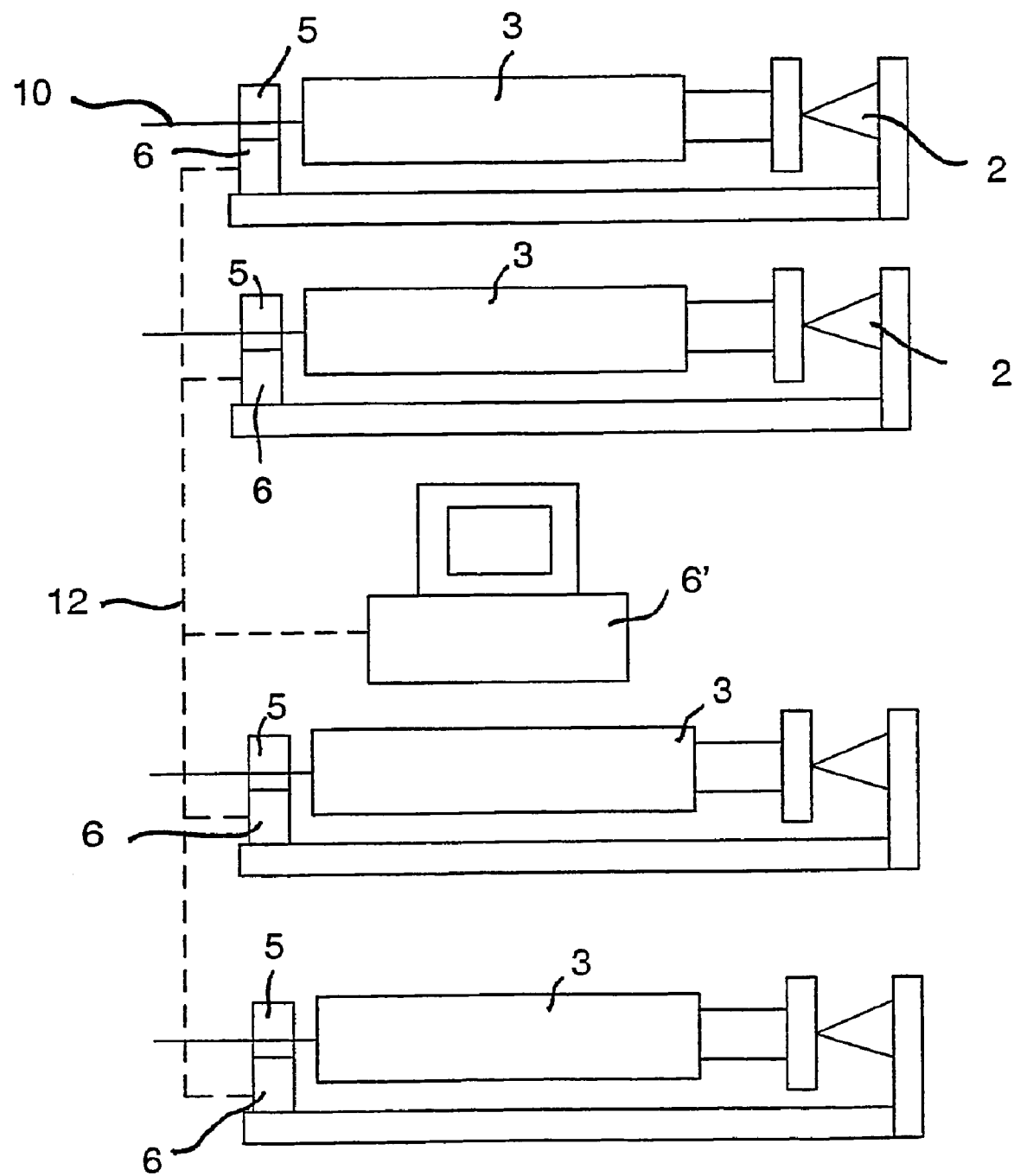
FIG. 3 the controlling of several pump systems by a computer.
Figures 14, 15:
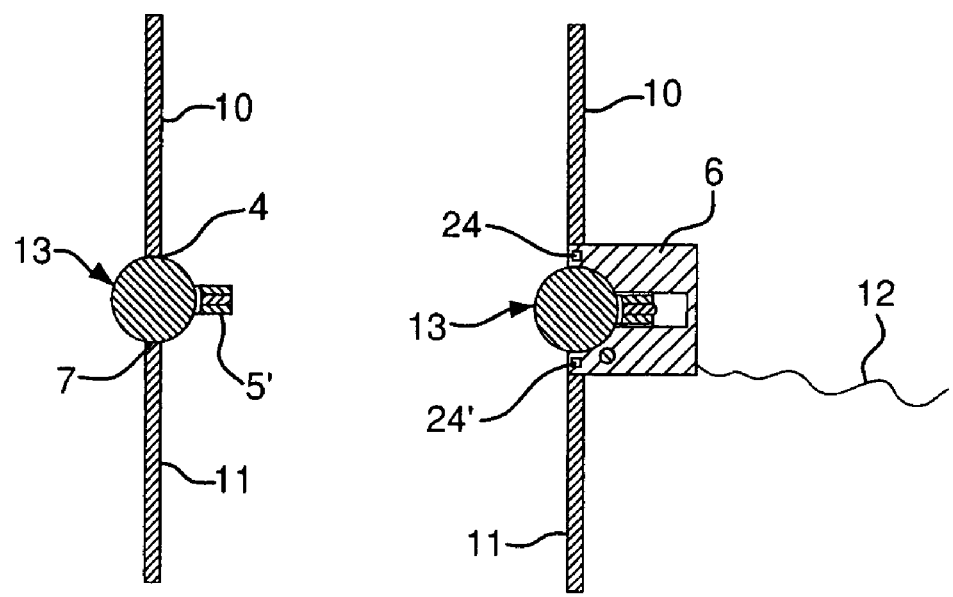
FIG. 14 schematically a pump device with its driver part.
FIG. 15 an embodiment of the pump device with seals at the housing and at the stopcock.

FIG. 14 illustrates schematically once again the pump device with portions of the inlet and outlet conduits and with the pump part 5' once without drive unit and once with a affixed drive unit 6 which is supplied with energy and signals through the conduit 12, which supplies the corresponding movement of the drive unit for controlling the pump part and the rotary valve. This drive unit or pump driver, respectively can be thereby affixed by mounting means simply at the pump unit and rotary valve. It moves the corresponding elements e.g. by means of two step motors and may include e.g. a air bubble detector 24 for the inlet connector and preferably a pressure sensor unit 24' in the outlet connector in order to detect occlusions in the conduit 11. Also, a pressure sensor unit is possible at the feeding connector which e.g. can announce a empty infusion source in time (before air is aspirated or a occlusion in the feeding conduit could be announced). The described pump device is such as illustrated in the FIGS. 1 to 3 combined with a infusion syringe driver or a infusion container. FIG. 1 illustrates thereby schematically the pump device according to the invention with a infusion syringe driver with corresponding infusion conduits. The device is mounted in the infusion conduit and is connected to the filled infusion syringe (regarding the possibilities reference is made to the already mentioned various possibilities). In this embodiment the infusion syringe is clamped onto a mount or slide, respectively with pressure spring which exerts a dosed uniform pressure onto the infusion syringe in order to support the pump device during the filling and to save electrical energy. The FIG. 1 illustrates the pump device with the driving unit. FIG. 2 illustrates the pump device on the basis of a infusion bag/bottle system with infusion conduits, whereby a droplet chamber is foreseen which serves for separating air. The pump device is mounted in the infusion conduit which is inserted into the infusion bottle/bag, whereby the droplet chamber is filled as conventional by a manual squeezing during which the infusion conduit is closed towards the lower side such that no air is aspirated from below. Thereafter the pump device is brought by the operator or operating the control unit 6', respectively and correspondingly the drive unit 6 into the rinsing position so that a free flow through the pump is possible and the infusion conduit is rinsed by infusion solution and air is cleaned off. Thereafter, the pumping operation is initiated. Alternatively the pump can be brought also manually into the through flow position as long as the drive unit has not yet been set on the pump device. In this case this takes place after the rinsing. FIG. 3 illustrates schematically several pump systems with infusion syringe drivers and pump units/drive units 5/6, which each are not controlled by a single control unit 6', but are attended to, controlled and monitored by a central control unit, e.g. a PC trough several control-cables 12. The pump device according to the invention includes preferably a display facility, e.g. at the drive unit 6 and/or the control unit 6'. The medicament and/or the flow rate should be recognizable at the display device. At a controlling by a computer (FIG. 3) these informations are preferably displayed additionally (or also only) on the monitor of the computer.

Figure 16:
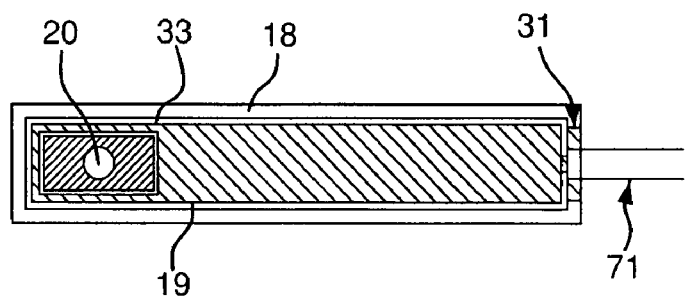
FIG. 16 a side-view of the pump device of FIG. 15.
Figure 17:
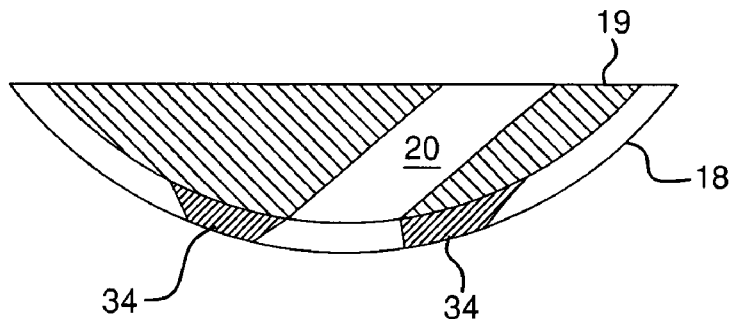
FIGS. 17-19 detailed views of the seals in various positions of the pump device.
Figure 18:
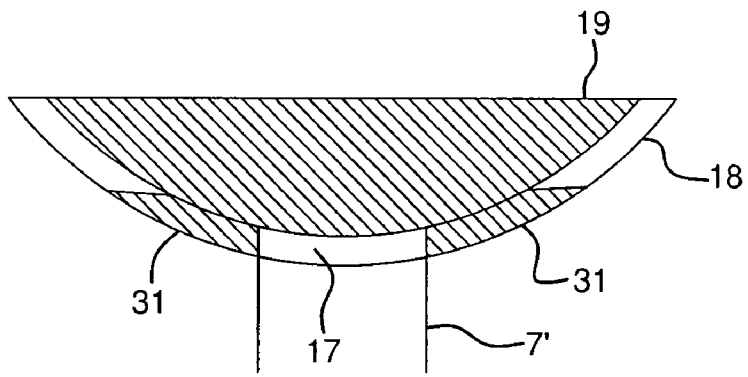
Figure 19:
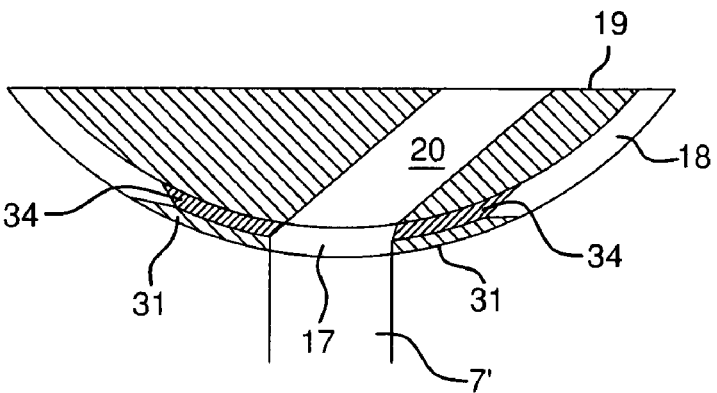

FIG. 15 illustrates a further schematic partly sectioned view of the pump device, whereby with reference to same various seals will be described which include at the one hand stationary seals 30, 31 and 32 mounted to the valve housing 18, which seals are located in the respective openings in the valve housing, as well as seals 33 and 34 which are located at the respective ends of the channel 20 of the elements 19 and which move together with the element 19. FIG. 16 illustrates a corresponding side view in which one of the moveable seals as well as one stationary seal in the valve housing are depicted. The FIGS. 17 and 18 illustrate detailed views of the respective seals whereby their chamfer and rounding are shown which allow a as much as possible low friction sliding of the element 19 in the valve housing 18. FIG. 19 illustrates, finally, the position in which the channel 20 of the element 19 is aligned with one of the housing openings of the pump housing, whereby the respective seals come to lie on top of each other and deform correspondingly. Accordingly, elastic known sealing materials are used which are resistant against the infusion solution. Because the illustrated valve part of the pump device is as a rule designed as throw away part, onto which the driving unit 6 is docked, the usable life time of the seals forms poses no problems.

Figure 20:
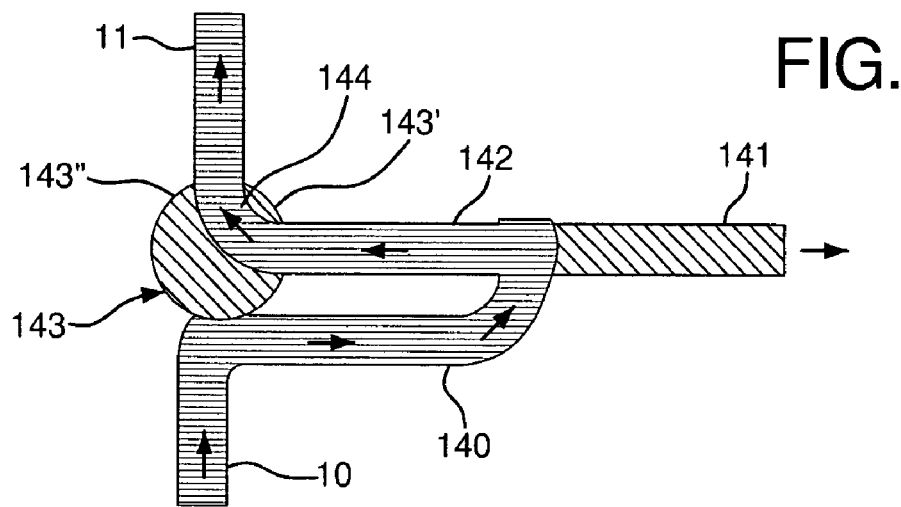
FIGS. 20, 21 and 22 a further embodiment of the pump device.
Figure 21:
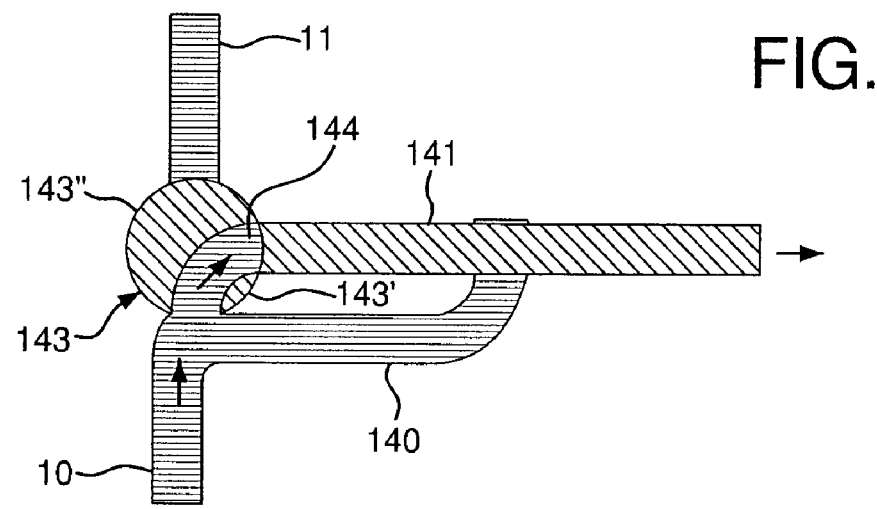
Figure 22:
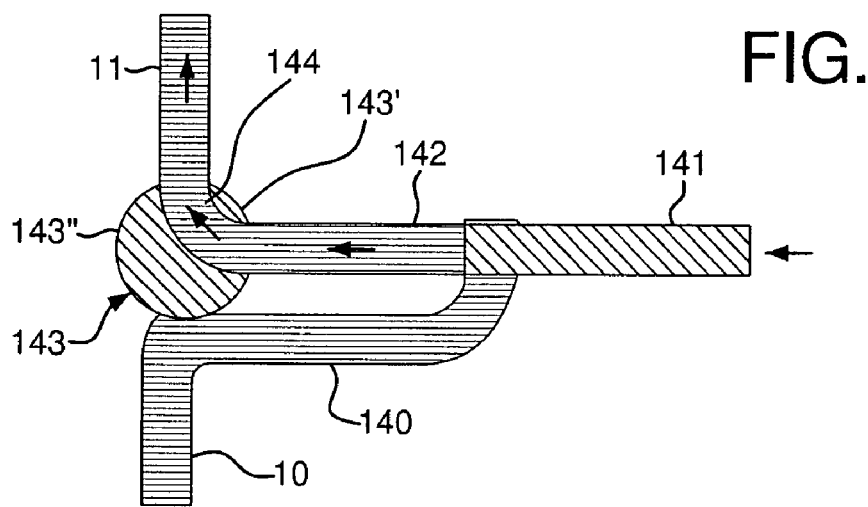

The FIGS. 20, 21 and 22 illustrate a further embodiment of the pump unit of the pump device, whereby also here the conduit 10 is located at the inlet side and is connected to the not illustrated inlet connector of the pump unit, whereas the conduit 11 is connected to the not illustrated outlet connector. A rinsing conduit 140 is foreseen in the unit, a driven moveable piston 141 forms together with a part of the conduit 142 in the pump unit a chamber, and the rotatable element 143 controls the rinsing and the filling and emptying of the chamber. This rotatable element 143 which is located in a not illustrated cylinder shaped housing with corresponding openings 14, 17, 21 for the conduits 10, 11 and the chamber 142, respectively, can be integral and form itself the curvilinear conduit portion 144. However, also two separate parts 143' and 143" may be foreseen which form together the element 143 and have a respective own drive; these parts 143' and 143" form then together the conduit portion 144.

With the rotatable element 143, the volumetric piston pump 141 and the rinsing system 140 all air bubbles can be removed along the path source of the infusion-infusion syringe and the bearings of the pump piston can be wetted by the medicament-liquid. By a combination of two such pump units a practically constant pump output can be ensured.

Rinsing position: FIG. 20: The element 143 is rotated towards the left. The pump piston 141 is pulled far out towards the right and enables the path between infusion source and injection syringe, or conduit 10 and conduit 11. The path is vented and the pump piston bearing is welted. All air can be removed here. In this position liquid can be aspirated through conduit 11 if required.

Pumping position: The element remains in the left rotary position (FIG. 22). The piston 141 is pushed in towards the left, so that liquid can be pressed out quits well dosed in the direction conduit 11. The piston has, thereby, closed the rinsing conduit 140. The liquid is fed quite well dosed in the direction conduit 11.

Thereafter, the element is rotated towards the right (FIG. 21). The piston can aspirate the medicament liquid from the conduit 10. It is to be noted, thereby, that it is pulled inwards only that far that the rinsing conduit always remains shut. This remains like this during the pumping operation until again a rinsing is desired.

The aspirating and feeding of the medicament to the patient can proceed at various speeds. If two such pump units are combined one unit can feed the medicament with the desired speed whereas the other unit, the element 143 rotated towards the right, aspirates liquid and the element, again rotated to the left, is in a standby state in order to be ready for its feeding when the first unit has pressed out by the piston the entire liquid. By means of this a more or less continuous medicament flow can be ensured.

The pump piston 141 and the element inner part 143 should be made of a harder material. The piston cylinder 142 or chamber, respectively as well as the element bushings (housing) are made advantageously of a somewhat softer but stiffer material. The element and piston seat is, thereby, to selected in such a manner that the seal is a good as possible, but the frictional resistance as well as the wear debris become as small as possible. In order to avoid a endangering of the patient by the wear debris the used materials are selected as much as possible bio-compatible.

Following advantages of this embodiment result:

The piston 141 and the element 143 can be moved independent from each other. Thereby all three phases: Rinsing, aspirating and ejecting are faultlessly separable from each other.

Only one seal in radial direction is needed for piston and element. This can be optimized by a suitable selection of the diameter of the element of the piston and the bushings surrounding same, as well as of the materials. No additional contact pressure is necessary.

The rotating element allows a volume precise pumping from the begin until the end of the pump stroke. By the combination of two such pumps a almost continuous pump output can be ensured.

The pump can feed liquids in both directions (from the infusion source to the injection needle and vice versa).

The system is closed. No liquid exits and no air is aspirated from the surroundings.

The merely periodic movements of the element (no rotation more than 90 degrees necessary; but possible) and the piston allow, furthermore, to seal the system airtight and sterile against the environment.

The relatively simple and rugged design allow a cost-efficient design.

LITERATURE

1) Cook R I. Syringe pump assemblies and the natural history of clinical technology (2000) CAn J Anesth 47: 929-935.

2) Lönnqvist P A (2000) How continuous are continuous drug infusions? Intensive Car Medicine 26:660-1.

3) Krauskopf K H, Rascher J, Brandt L (1996) Störung der kontinuierlichen, pumpengesteuerten Applikation kardiovaskulär wirksamer Pharma durch den hydrostatischen Druck. Anaesthesist 45: 449-452.

4) Lönnqvist P A, Löfqvist B (1997) Design flaw can convert commercially available continuous syringe pumps to intermittent bolus injectors. Intensive Care Med 23: 9989-1001.

5) Weiss M, Baenziger O, Neff T, Fanconi S (2000) Influence oif infusion line compliance on drug delivery during acute line loop formation. Intensive Care Medicine 26: 776-779.

6) Weiss M, Fischer J, Neff T, Baenziger O (2000) Syringe plunger design affects drug delivery from syringe infusion pumps. Anaesthesia 55: 1094-1098.

7) Neff T, Fischer J, Schulz G, Baenziger O, Weiss M (2001) Infusion pump performance with vertical displacement: effect of syringe pump and assembly type. Intensive Care Medicine 27: 287-291.

8) Weiss M, Hug M I, Neff T, Fischer J (2000) Syringe size and flow rate affect drug delivery from syringe pumps. Canadian Journal of Anesthesia 47: 1031-1035.

9) Weiss M, Fischer J, Schulz G, Neff T, Baenziger O (2000) Do antisiphon valves reduce flow irregularities of syringe pumps? Anaesthesia and Intensive Care 28: 680-683.

10) Kim D W, Steward D J (1999) The effect of syringe size on the performance of an infusion pump. Paediatric Anaesthesia 9: 335-7.

11) Weiss M, Neff T, Fischer J, Gerber A C (2000) The effect of infusion line compliance on syringe pump performance. Paediatric Anaesthesia 10: 595-599.

12) Schulz G, Fischer J, Neff T, Baenziger O, Weiss M (2000) Der Einfluss von Lufteinschluss in der Infusionsspritze auf die Funktion von Spritzenpumpen. Anaesthesist 49: 1018-1023.

13) Neff T, Fischer J, Fehr S, Baenziger O, Weiss M (2001) Start-up delays of syringe infusion pumps. Paediatric Anaesthesia, in press.

14) Neff T, Fischer J, Fehr S, Baenziger O, Weiss M (2001) Evaluation of the FASTSTART mode for reducing start-up delay in syringe pump infusion systems. Swiss Medical Weekly; in press.

15) McCarroll C, McAtamney D, Taylor R (2001) Alteration in flow delivery with antisyphon devices. Anaesthesia 55:355-357.

16) Capes D F, Dunster K R, Sunderland V B et al. Fluctuations in syringe pump infusion systems: Association with blood pressure variations in infants. Am J Health-Syst Pharm 1995; 52: 1646-1653.

The invention claimed is:

1. A medical pump device, comprising:
   an inlet connector arranged for connecting a first fluid conduit to the medical pump device;
   an outlet connector arranged for connecting a second fluid conduit to the medical pump device;
   a pump part comprising at least one chamber wall moveable between forward and retracted positions within a pump chamber, such that when the at least one chamber wall moves from the forward position to the retracted position the pump chamber is filled with fluid from the inlet connector and when the at least one chamber wall moves from the retracted position to the forward position the pump chamber is emptied through the outlet connector; and
   a rotary valve assembly comprising a rotary valve housing with three openings each corresponding with one of the inlet connector, the outlet connector, and the pump chamber, the rotary valve including a rotary valve element provided with only a straight channel having a substantially constant thickness for limiting adherence of air bubbles within the housing during a rinsing operation, the straight channel being arranged to correspond with two of the openings at a time depending on the position of the rotary valve element for a selectable fluid communication between the inlet connector, the outlet connector, and the pump chamber,
   wherein the openings are arranged uniformly in the rotary valve housing and staggered by 120°,
   wherein an opening of the pump chamber is directly connected to one of the three openings of the rotary valve housing,
   wherein a front end of the at least one chamber wall of the pump part is shaped to conform with an outer contour of the rotary valve element, and
   wherein only the straight channel of the rotary valve element is utilized for the filling of the pump chamber, the emptying of the pump chamber, and the rinsing operation of the medical pump device.

2. A medical pump device according to claim 1, wherein the pump chamber includes at all sides rigid chamber walls of which the at least one chamber wall is arranged movably.

3. A medical pump device according to claim 2, wherein the at least one chamber wall is formed by the piston or plunger.

4. A medical pump device according to claim 2, wherein the at least one chamber wall is formed by a elastic or quasi-rigid membrane which acts as rigid chamber wall so that it is completely acted upon by a non-compressible acting medium.

5. A medical pump device according to claim 1, further comprising a detachable drive assembly.

6. A medical pump device according to claim 1, further comprising elastic sealing elements located in at least one of the channel or housing of the rotary valve assembly.

7. A medical pump system, comprising:
   an infusion member having an outlet;
   a medical pump connected to the infusion member outlet, comprising:
      an inlet connector arranged for connecting a first fluid conduit to the medical pump;
      an outlet connector arranged for connecting a second fluid conduit to the medical pump;
      a pump part comprising at least one chamber wall moveable between forward and retracted positions within a pump chamber, such that when the at least one chamber wall moves from the forward position to the retracted position the pump chamber is filled with fluid from the inlet connector and when the at least one chamber wall moves from the retracted position to the forward position the pump chamber is emptied through the outlet connector; and
      a rotary valve assembly comprising a rotary valve housing with three openings each corresponding with one of the inlet connector, the outlet connector, and the pump chamber, the rotary valve including a rotary valve element provided with only a straight channel having a substantially constant thickness for limiting adherence of air bubbles within the housing during a rinsing operation, the straight channel being arranged to correspond with two of the openings at a time depending on the position of the rotary valve element for a selectable fluid communication between the inlet connector, the outlet connector, and the pump chamber, and wherein the openings are arranged uniformly in the rotary valve housing and staggered by 120°,
   wherein an opening of the pump chamber is directly connected to one of the three openings of the rotary valve housing, and
   wherein only the straight channel of the rotary valve element is utilized for the filling of the pump chamber, the emptying of the pump chamber, and the rinsing operation of the medical pump.

8. A medical pump device according to claim 7, wherein a front end of the at least one chamber wall is shaped to conform with an outer contour of the rotary valve element.

* * * * *

UNITED STATES PATENT AND TRADEMARK OFFICE
CERTIFICATE OF CORRECTION

PATENT NO.       : 7,614,857 B2                                               Page 1 of 1
APPLICATION NO.  : 10/495462
DATED            : November 10, 2009
INVENTOR(S)      : Fuechslin et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 561 days.

Signed and Sealed this

Nineteenth Day of October, 2010

David J. Kappos
*Director of the United States Patent and Trademark Office*